(12) United States Patent
Shultz et al.

(10) Patent No.: US 11,633,548 B2
(45) Date of Patent: Apr. 25, 2023

(54) DRUG INJECTION DEVICE WITH VISUAL AND AUDIO INDICATORS

(71) Applicant: AMGEN INC., Thousand Oaks, CA (US)

(72) Inventors: Peter V. Shultz, Woodland Hills, CA (US); Christopher R. Folk, San Diego, CA (US); Sigrid Moeslinger, New York, NY (US); Masamichi Udagawa, New York, NY (US); Molly Evans, Laguna Beach, CA (US); Lin Gao, Los Angeles, CA (US); Lisa Nugent, Malibu, CA (US)

(73) Assignee: AMGEN INC., Thousand Oaks, CA (US)

( * ) Notice: Subject to any disclaimer, the term of this patent is extended or adjusted under 35 U.S.C. 154(b) by 330 days.

(21) Appl. No.: 15/930,018

(22) Filed: May 12, 2020

(65) Prior Publication Data
US 2020/0390982 A1  Dec. 17, 2020

Related U.S. Application Data

(63) Continuation of application No. 15/501,953, filed as application No. PCT/US2015/055523 on Oct. 14, 2015, now Pat. No. 10,695,506.

(Continued)

(51) Int. Cl.
*A61M 5/32* (2006.01)
*A61M 5/50* (2006.01)
(Continued)

(52) U.S. Cl.
CPC ........... *A61M 5/3257* (2013.01); *A61B 50/33* (2016.02); *A61M 5/3134* (2013.01);
(Continued)

(58) Field of Classification Search
CPC .......... A61M 5/3134; A61M 5/5086
See application file for complete search history.

(56) References Cited

U.S. PATENT DOCUMENTS 5,984,899 A  11/1999  D'Alessio et al.
2004/0167476 A1*  8/2004  Westbye ............. A61M 5/3271
604/192
(Continued)

FOREIGN PATENT DOCUMENTS

WO  WO-99/11306 A1  3/1999
WO  WO-2006111864 A1  10/2006
(Continued)

OTHER PUBLICATIONS

European Patent Application No. 21150456.8, Extended European Search Report, dated May 31, 2022.
(Continued)

*Primary Examiner* — Bradley J Osinski
(74) *Attorney, Agent, or Firm* — Marshall, Gerstein & Borun LLP

(57) ABSTRACT

A drug injection device (10) including a housing (12) for holding a container (20) having a needle (24) for penetrating skin and a plunger (42) for expelling a drug stored in the container. The device includes visual and/or audible indicators for indicating that the correct depth of needle penetration has been achieved and that drug injection/extrusion has been started and/or completed. The device may further include a label (140) for visually confirming the quality of the drug contained therein. Alternatively, a tray (110) may be provided for receiving the drug injection device, which allows the quality of the drug contained therein to be visually confirmed.

13 Claims, 10 Drawing Sheets

Related U.S. Application Data

(60) Provisional application No. 62/063,737, filed on Oct. 14, 2014.

(51) Int. Cl.
    *A61B 50/33*     (2016.01)
    *A61M 5/31*     (2006.01)

(52) U.S. Cl.
    CPC ........ *A61M 5/3245* (2013.01); *A61M 5/5086* (2013.01); *A61M 2005/3263* (2013.01); *A61M 2005/3267* (2013.01); *A61M 2205/581* (2013.01); *A61M 2205/583* (2013.01)

(56) References Cited

U.S. PATENT DOCUMENTS

| | | | |
|---|---|---|---|
| 2005/0038387 A1 | 2/2005 | Kriesel et al. | |
| 2006/0247579 A1* | 11/2006 | Friedman | A61M 5/2033 604/197 |
| 2013/0317432 A1 | 11/2013 | Fabien et al. | |
| 2014/0058333 A1 | 2/2014 | Cross et al. | |
| 2014/0257200 A1 | 9/2014 | Auerbach et al. | |
| 2014/0357304 A1* | 12/2014 | Ostrander | H04W 4/023 455/456.3 |
| 2015/0265782 A1 | 9/2015 | Riedel et al. | |

FOREIGN PATENT DOCUMENTS

| | | |
|---|---|---|
| WO | WO-2013/041642 A1 | 3/2013 |
| WO | WO-2014/053496 A1 | 4/2014 |
| WO | WO-2014/060214 A1 | 4/2014 |
| WO | WO-2014060563 A2 | 4/2014 |

OTHER PUBLICATIONS

Canadian Patent Application No. 2957960, Office Action, dated Nov. 15, 2021.
European Patent Application No. 21150456.8, Partial European Search Report, dated Dec. 7, 2021.
Australian Patent Application No. 2015332557, Examination Report No. 1, dated Sep. 13, 2019.
International Preliminary Report on Patentability and Written Opinion of the International Searching Authority, International Application No. PCT/US2015/055523, dated Apr. 18, 2017.
International Search Report, International Application No. PCT/US2015/055523, dated Apr. 7, 2016.
Japanese Patent Application No. 2017-519830, Notice of Rejection, dated Jul. 30, 2019.
Written Opinion of the International Searching Authority, International Application No. PCT/US2015/055523, dated Apr. 7, 2016.

* cited by examiner

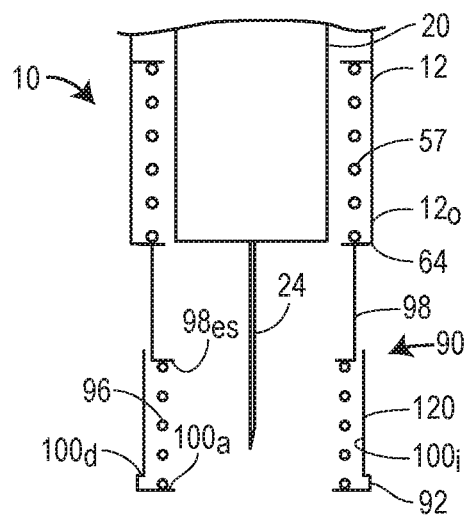
FIG. 6A
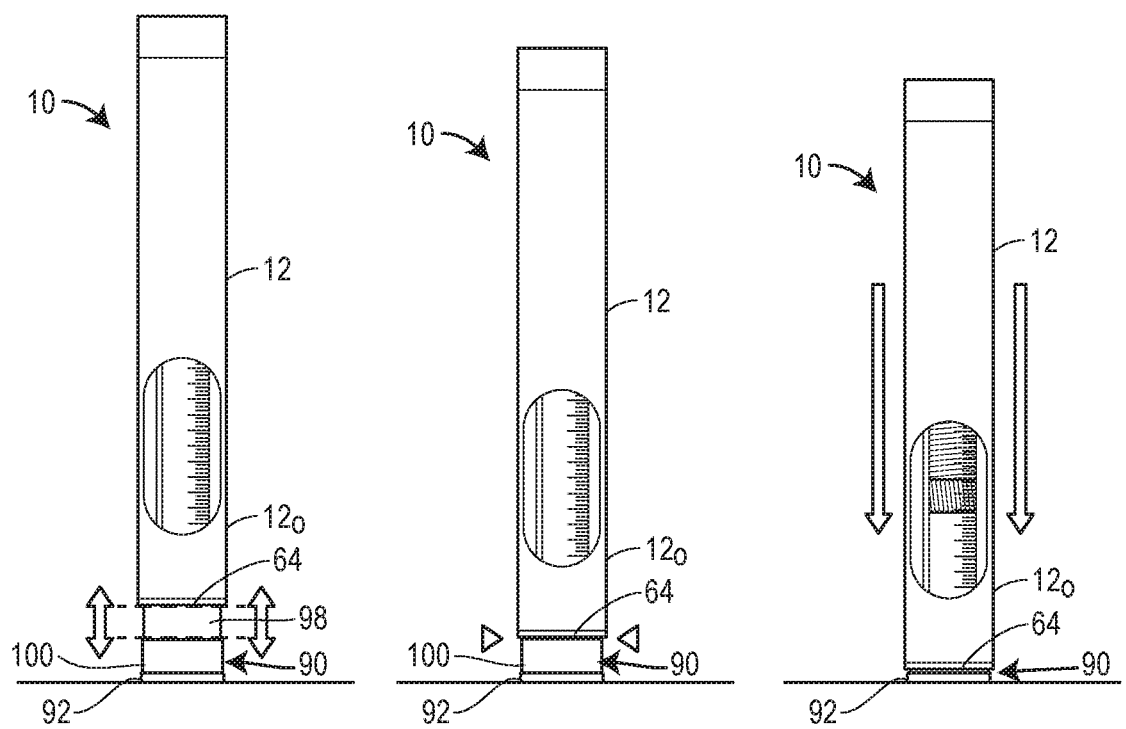
FIG. 6B  FIG. 6C  FIG. 6D

DRUG INJECTION DEVICE WITH VISUAL AND AUDIO INDICATORS

CROSS-REFERENCE TO RELATED APPLICATIONS

This application is a continuation of U.S. patent application Ser. No. 15/501,953, filed Feb. 6, 2017, which is the United States national phase of International Patent Application No. PCT/US2015/055523, having an international filing date of Oct. 14, 2015, which claims the priority benefit of U.S. Provisional Patent Application No. 62/063,737, filed Oct. 14, 2014, which are all hereby incorporated by reference herein in their entireties.

FIELD OF THE DISCLOSURE

The present disclosure relates to drug delivery devices. More particularly, the present disclosure relates to a drug delivery or injection device having visual and audible indicators associated with one or more of needle penetration, drug delivery, drug quality, and injector orientation.

BACKGROUND

There are many diseases and conditions which may require a patient to inject themselves with a drug. Accordingly, drug injection devices such as autoinjectors, injection pens, and the like, have been developed to permit a patient or user to conveniently and accurately self-administer proper doses of a drug.

In some injection devices, the injection needle may be fixed relative to the primary container, therefore, the patient or user must apply a force to pierce the skin to deliver the drug. Once the injection needle has achieved the required depth of penetration, which is typically controlled by the patient or user, a drive mechanism advances a plunger which delivers the drug contained in the primary container through the injection needle.

Since the patient or user is responsible for the penetration depth, it would be helpful to the patient or user if the drug injection device had some way of indicating to the patient or user when the correct depth has been achieved. It would also be helpful if the drug injection device could indicate to the patient or user when other stages of the injection process are occurring or have occurred and/or other information, which facilitate the convenient and accurate use of the device.

SUMMARY

Disclosed herein is a drug injection device. In various embodiment, the drug injection device can include a housing, a container, a needle guard, and at least one indicia on the needle guard. The container can be disposed within the housing and have a needle and a plunger. The container can be adapted to store a product for administration to a patient at an injection site. The plunger can be adapted to expel the product through the needle, wherein a portion of the needle extends out of the housing. The needle guard can be coupled to the housing adjacent to the needle of the container. The needle guard can be movable relative to the housing between (a) a fully extended position wherein the needle guard extends from the housing and beyond the portion of the needle extending out of the housing, (b) an intermediate position wherein the needle guard extends from the housing approximately the same distance that the needle extends out of the housing, and (c) a fully retracted position wherein a substantial portion of the needle extending out of the housing is exposed beyond the needle guard. The at least one indicia disposed on the needle guard is for providing a visual indication of the position of the needle relative to the injection site based on a position of the needle guard relative to the housing.

In various embodiments, the at least one indicia can include at least one of the following: (a) a color, (b) a text-based indicia, (c) an image, (d) a symbol, (e) a graphic, (f) a pattern, (g) an illuminated visual indicator.

In various embodiments, the device can further include at least one spring biasing the needle guard toward the fully extended position.

In various embodiments, the needle guard can include a unitary hollow cylindrical member.

In various embodiments, the needle guard can include an outer surface including a proximal outer surface portion and a distal outer surface portion such that (a) when the needle guard occupies the fully extended position, the proximal and distal outer surface portions are exposed outside of the housing, (b) when the needle guard occupies the intermediate position, the proximal outer surface portion is concealed inside the housing and the distal outer surface portion is exposed outside of the housing, and (c) when the needle guard occupies the fully retracted position, the proximal and distal outer surface portions are concealed inside the housing.

In various embodiments, the at least one indicia can include a first indicia disposed on the proximal outer surface portion and a second indicia disposed on the distal outer surface portion, the first indicia being visually distinct from the second indicia.

In various embodiments, the needle guard can include first and second needle guard members telescopically movable relative to each other.

In various embodiments, the first needle guard member can include a first outer surface and the second needle guard member includes a second outer surface such that (a) when the needle guard occupies the fully extended position, the first and second outer surfaces are exposed outside of the housing, (b) when the needle guard occupies the intermediate position, (i) the second outer surface is concealed inside the first needle guard member and the first outer surface is exposed outside of the housing, or (ii) the first outer surface is concealed inside the second needle guard member and the second outer surface is exposed outside of the housing, and (c) when the needle guard occupies the fully retracted position, the first and second outer surfaces are concealed inside the housing.

In various embodiments, the at least one indicia can include a first indicia disposed on the first outer surface of the first needle guard member, and a second indicia disposed on the second outer surface of the second needle guard member, the first indicia being visually distinct from the second indicia.

In various embodiments, the device can further include a first biasing member disposed between the housing and the first needle guard member, the first biasing member biasing the first needle guard member away from the housing, and a second biasing member disposed between the first and second needle guard members, the second biasing member biasing the second needle guard member away from the first needle guard member.

In various embodiments, the first biasing member generates a biasing force greater than a biasing force generated by the second biasing member.

In various embodiments, the needle guard can further include an outer rim disposed in engagement with the housing when the needle guard occupies the fully retracted position, thereby limiting further retraction of the needle guard into the housing.

In various embodiments, the at least one indicia includes indicia disposed on the outer rim.

In various embodiments, the device can further include an audible indicator associated with the needle guard and configured to generate an audible signal when (a) the needle guard moves to the intermediate position from the fully extended position and/or (b) the needle guard moves to the fully retracted position from the intermediate position.

In various embodiments, the housing can include at least one window or transparent section that allows viewing of the container and/or plunger in the housing.

In various embodiments, the device can further include a temperature indicator carried by the housing and adapted for indicating a temperature of a product in the container.

The disclosure also provides a tray for a drug injection device having a housing for holding a container storing a drug therein, wherein the housing including a window that allows viewing of the drug, the window comprising (a) one or more discrete windows in the housing of the drug injection device, or (b) a transparent 360 degree section of the housing of the container. The tray can include a support wall and a drug test surface. The support wall defines a first recess adapted to hold the drug injection device. The drug test surface can be disposed on the support wall, such that at least a portion of the drug test surface is disposed in the recess immediately adjacent the window of the drug injection device when the drug injection device is disposed in the tray. So configured, the drug in the container can be compared against the drug test surface to determine at least one of a clarity and a color of the drug by viewing the drug against the drug test surface through the window of the housing of the device.

In various embodiments, the drug test surface can be disposed under the section of the housing of the device including the window if the device is disposed in the first recess.

In various embodiments, the drug test surface can include an area of a first color for testing one of the clarity and the color of the drug.

In various embodiments, the drug test surface can include an area of a second color for testing the other one of the clarity and the color of the drug.

In various embodiments, the drug test surface can include an instruction to determine the at least one of the clarity and the color of the drug.

In various embodiments, the tray may further include a second recess extending transverse to the first recess to allow for removal of the drug injection device from the tray.

The disclosure also provides a drug injection device including a housing and a removable label. The housing is for holding a container storing a drug therein, the housing including a window that allows viewing of the drug in the container, wherein the window comprises (a) one or more discrete windows in the housing of the drug injection device, or (b) a transparent 360 degree section of the housing of the container. The removable label is disposed over the housing. The label can have first and second sections, the second section of the label having an inner surface that defines a drug test surface disposed immediately adjacent to at least a portion of the window in the housing. So configured, removal of the first section of the label from the housing allows at least one of a clarity and a color of the drug to be determined by comparing the drug with the drug test surface of the second section of the label by viewing the drug through the window against the drug test surface.

In various embodiments, the drug test surface includes an area of a first color for testing one of the clarity and the color of the drug.

In various embodiments, the drug test surface includes an area of a second color for testing the other one of the clarity and the color of the drug.

In various embodiments, the first section of the label has a first instruction to remove the first section to check the drug and a second instruction to determine the at least one of the clarity and the color of the drug.

In various embodiments, the label further includes a third section having a first instruction to remove the third section of the label if the at least one of the clarity and the color of the drug is determined to be proper and a second instruction to not use the device if the at least one of the clarity and the color of the drug is determined to be improper.

In various embodiments, the label includes a pull tab.

In various embodiments, the container includes a needle for penetrating skin and dispensing the drug stored in the container, at least a portion of the needle extending out of the housing and further includes a cap for enclosing the at least portion of the needle; wherein the label at least partially covers the cap.

Yet various other embodiments of the drug injection device may comprise a housing for holding a container. The container may have a needle and a plunger, the needle for penetrating skin and the plunger for expelling a drug stored in the container through the needle, at least a portion of the needle extending out of the housing. A driver may be associated with the housing for driving the plunger through the container. A needle guard may extend beyond the housing to enclose the at least portion of the needle extending out of the housing.

In various embodiments, an injection process may be commenced by placing the needle guard of the device into contact with skin at an injection site and advancing the device towards the skin.

In various embodiments, the needle guard may move in the direction of the housing as the device is advanced towards the skin to visually indicate when the needle begins to penetrate the skin.

In various embodiments, as the needle guard moves in the direction of the housing, at least a portion of the needle guard may be at least partially concealed to provide the visual indication.

In various embodiments, the drug injection device may further comprise an audible indicator associated with the needle guard to audibly indicate when the needle begins to penetrate the skin.

In various embodiments, the drug injection device may further comprise an audible indicator associated with the needle guard to audibly indicate when the plunger begins to expel the drug from the container.

In various embodiments, the drug injection device may further comprise an audible indicator associated with the needle guard to audibly indicate when the plunger has completed expelling the drug from the container.

In various embodiments, the needle guard may be biased in an extended position.

In various embodiments, the needle guard may include color-based indicia for visually indicating when the needle begins to penetrate the skin.

In various embodiments, the needle guard may include text-based indicia for visually indicating when the needle begins to penetrate the skin.

In various embodiments, the needle guard may include color- and text-based indicia for visually indicating when the needle begins to penetrate the skin.

In various embodiments, the housing may have an elongated body comprising first and second ends, wherein the first end of the body may have a first shape and the second end of the body may have a second shape, which is different from the first shape to distinguish the first and second ends of the body from one another.

In various embodiments, the shape of the body may gradually change from the first shape to the second shape.

In various embodiments, at least one of the first and second shapes may include a flat or substantially surface to prevent the device from rolling when placed on a support surface.

In various embodiments, one of the first and second ends of the body may comprise a removable cap that encloses the needle guard.

In various embodiments, the housing may include at least one window that allows viewing of the plunger, the plunger visually indicating when the injection process has been completed.

In various embodiments, the at least one window may comprise a lens that magnifies the view of the plunger through the at least one window.

In various embodiments, the housing may include a transparent section that allows 360 degrees of viewing of the plunger, the plunger visually indicating when the injection process has been completed.

In various embodiments, the transparent section of the housing may include a lens that magnifies the view of the plunger through the transparent section of the housing.

In various embodiments, the plunger may have a vivid color to facilitate the viewing thereof In various embodiments, the drug injection device may further comprise a temperature indicator.

In various embodiments, the drug injection device may further comprise a label with non-slip features, the label attached to the housing.

In various embodiments, the needle guard includes first color-based indicia for visually indicating when the needle begins to penetrate the skin and second color-based indicia for visually indicating when the plunger begins to expel the drug from the container.

In various embodiments, the needle guard may move in the direction of the housing as the device is advanced towards the skin to visually indicate when the needle begins to penetrate the skin and when the plunger begins to expel the drug from the container.

In various embodiments, as the needle guard moves in the direction of the housing, a first portion of the needle guard may be concealed to provide one of the visual indications and a second portion or the entire needle guard may be concealed to provide the other one of the visual indications.

In various embodiments, the needle guard may include first text-based indicia for visually indicating when the needle begins to penetrate the skin and second text-based indicia for visually indicating when the plunger begins to expel the drug from the container.

In various embodiments, the needle guard may include first color- and first text-based indicia for visually indicating when the needle begins to penetrate the skin and second color and second text-based indicia for visually indicating when the plunger begins to expel the drug from the container.

In various embodiments, the needle guard may include first and second needle guard members, wherein the first and second needle guard members of the needle guard may sequentially move in the direction of the housing as the device is advanced towards the skin to visually indicate when the needle begins to penetrate the skin.

In various embodiments, as one of the first and second needle guard members move in the direction of the housing it may be concealed to provide the visual indication.

In various embodiments, the sequential movement of the first and second needle guard members of the needle guard may further visually indicate when the plunger begins to expel the drug from the container and wherein as one of the first and second needle guard members moves in the direction of the housing it may be concealed to provide one of the visual indications and as the other one of the first and second guard members moves in the direction of the housing may be at least partially concealed to provide the other one of the visual indications.

In various embodiments, the first and second needle guard members may each be biased in an extended position.

In various embodiments, one of the first and second needle guard members may include first color-based indicia and wherein the other one of the first and second needle guard members may include second color-based indicia.

In various embodiments, one of the first and second needle guard members may include first text-based indicia and wherein the other one of the first and second needle guard members may include second text-based indicia.

In various embodiments, one of the first and second needle guard members may include first color- and first text-based indicia and the other one of the first and second needle guard members may include second text-based indicia.

Further disclosed herein is a tray for a drug injection device having a housing for holding a container storing a drug therein, wherein the housing may include a window or a transparent housing section that allows viewing of the drug. Various embodiments of the tray may comprise a drug test surface for comparing the drug with to determine at least one of a clarity and a color of the drug by viewing the drug through the window or the transparent housing section.

In various embodiments, the tray may include a recess for holding the drug injection device, wherein the drug test surface may be disposed in the recess.

In various embodiments, the drug test surface may be disposed under the window or the transparent housing section if the device is disposed in the recess.

In various embodiments, the drug test surface may include an area of a first color for testing one of the clarity and the color of the drug.

In various embodiments, the drug test surface may include an area of a second color for testing the other one of the clarity and the color of the drug.

In various embodiments, the drug test surface may include an instruction to determine the at least one of the clarity and the color of the drug.

Further disclosed herein is a drug injection device, which comprises a removable label for confirming the quality of a drug contained in the device.

In various embodiments, the drug injection device may further comprise a housing for holding a container, the container storing a drug therein.

In various embodiments, the housing may include a window or a transparent housing section that allows viewing of the drug in the container.

In various embodiments, the removable label may be disposed over the housing.

In various embodiments, the label may have first and second sections, the second section of the label having an inner surface that defines a drug test surface, wherein removal of the first section of the label from the housing may allow at least one of a clarity and a color of the drug to be determined by comparing the drug with the drug test surface of the second section of the label by viewing the drug through the window or the transparent housing section.

In various embodiments, the inner drug test surface may include an area of a first color for testing one of the clarity and the color of the drug.

In various embodiments, the inner drug test surface may include an area of a second color for testing the other one of the clarity and the color of the drug.

In various embodiments, the first section of the label may have a first instruction to remove the first section to check the drug and a second instruction to determine the at least one of the clarity and the color of the drug.

In various embodiments, the label may further include a third section having a first instruction to remove the third section of the label if the at least one of the clarity and the color of the drug is determined to be proper and a second instruction to not use the device if the at least one of the clarity and the color of the drug is determined to be improper.

In various embodiments, the label may include a pull tab.

In various embodiments, the drug injection device may further comprise a cap which is at least partially covered by the label.

BRIEF DESCRIPTION OF THE DRAWINGS

FIG. 6A is a partial elevational view of a needle guard of the drug injection device according to another embodiment of the disclosure.

FIGS. 6B-6D are elevational views of the drug injection device showing the operation of the needle guard of FIG. 6A, according to an embodiment of the disclosure.

DETAILED DESCRIPTION

Figure 1A:
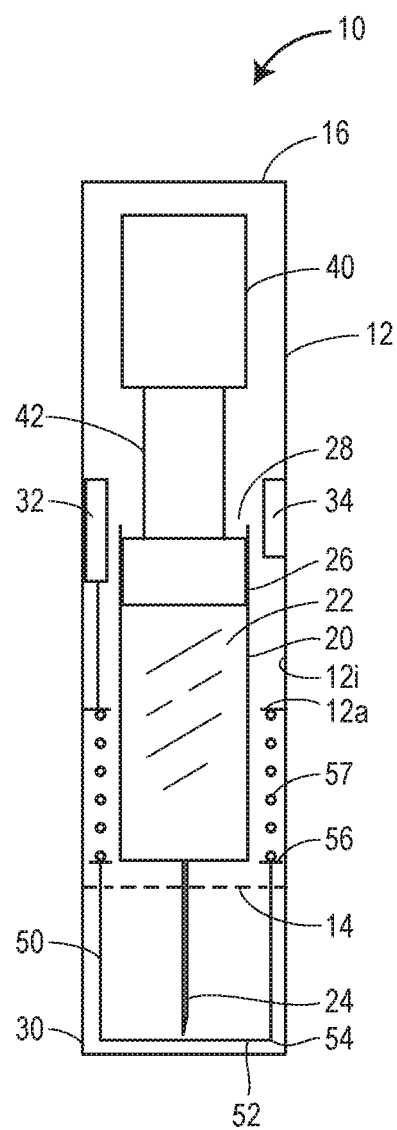
FIG. 1A is an elevational view of a drug injection device according to an embodiment of the disclosure, with certain elements of the device shown in cross-section.

FIG. 1A shows an embodiment of a drug injection device according to the present disclosure, denoted generally by reference numeral 10. In various embodiments, the drug injection device 10 may comprise an autoinjector for automatically delivering a subcutaneous injection of a fixed or user/patient-settable dose of a drug. Autoinjectors are often associated with a patient self-administering an injection, however, such an injection may also be administered by a health care provider. Similarly, use of the drug injection device may be undertaken by either the patient or health care provider.

As shown in FIG. 1A, the drug injection device 10 may be configured as a pen-type device. Some embodiments of the drug injection device 10 may be configured as a disposable, single use device which delivers a fixed dose of the drug. In other embodiments, the drug injection device 10 may be configured as a reusable device. Reusable drug injection devices 10 may be constructed to deliver a multiple doses of a drug where the doses of the drug may be fixed or user/patient-settable.

Referring still to FIG. 1A, the drug injection device 10 comprises a housing 12 having a distal end 14 and a proximal end 16. The housing 12 may have a generally elongated, tubular shape. The housing 12 may be open at the distal end 14 and closed at the proximal end 16. The housing 12 can be constructed as a single, unitary component or constructed from multiple components or sections that are combined into a single, integral unit. The housing 12 in pen-type devices may be dimensioned to hold a single primary container 20. In other embodiments, the housing 12 can be configured in other shapes and/or dimensioned to hold a plurality of primary containers. The primary container 20 may be pre-filled with a drug 22. The primary container 20 may comprise a glass or plastic syringe and may include an injection needle 24 through which the drug 22 can be injected into a patient. The injection needle 24 may be removably or non-removably secured to the primary container 20 and typically extends through the distal end 12 of the housing 12. A cap 30 may be removably connected to the distal end 14 of the housing 22 for covering the injection needle 24. The housings 12 of reusable devices may be configured to allow removal and insertion of the primary container 20.

The device 10 may be configured so that the primary container 20 is fixed relative to the housing 12 as shown in FIG. 1A. In such embodiments, the patient or user must apply a force to penetrate the skin with the injection needle 24 to deliver the drug 22. Various other embodiments of the device 10 may include a drive mechanism for moving the primary container 20 relative to the housing 12 to automatically penetrate the skin with the injection needle 24.

In still other embodiments, a portion or section of the housing may form the primary container (not shown). The primary container in such embodiments may be pre-filled with a drug. In such embodiments, the injection needle may be removably or non-removably connected to the distal end of the housing such that it communicates with the portion or section of the housing forming the primary container.

Referring again to FIG. 1A, the primary container 20 may contain a piston 26, which seals an open end 28 of the primary container 20. The piston 26 can be slidably driven through the container 20 to expel the drug 22 from the container 20 through the injection needle 24. A plunger 42 may be provided for driving the piston 26 through the container 20. The plunger 42 may extend into the open end 28 of the primary container 20 to directly or indirectly engage the piston 26. A drive mechanism 40 may be provided for automatically actuating the plunger 42. The primary container 20 may be transparent, partially transparent or translucent, to allow a patient or user to view the position of the plunger 42 within the container 20 as will be explained further on.

The drive mechanism 40 may comprise a mechanical arrangement of one or more springs or an electrical/mechanical arrangement comprising one or more motors and/or solenoids and a drive train or transmission. The drive mechanism 40 may include a microprocessor for controlling the drive mechanism 40. In some embodiments, the microprocessor may allow dose setting. In other embodiments a mechanical dose setting arrangement may be separately provided, which controls the distance that the drive mechanism 40 moves the piston 26 through the primary container 20 via the plunger 42, to allow the patient or user to set the dose.

Referring still to FIG. 1A, a needle guard 50 may be provided at the distal end 14 of the housing 20. The needle guard 50 is typically configured to surround the injection needle 24 to prevent accidental needle sticks when the device 10 is not being operated but when the cap 30 is removed. In the present embodiment, the needle guard 50 can include a unitary hollow cylindrical member, as depicted in FIG. 1A, for example. But other embodiments can take on different constructs, as will be described below, for example in reference to FIGS. 6A-6D and 7A-7D. In some embodiments, the needle guard 50 may also activate the drive mechanism 40 when the device 10 is pressed down onto the injection site, which causes the needle guard 50 to move proximally relative to the housing 12 from an extended position. Activation of the drive mechanism 40 by the needle guard 40 may be realized using any suitable mechanical arrangement, any suitable electrical arrangement, or any suitable combination of a mechanical and electrical arrangement. Because such arrangements are well known in the art, a further description of these arrangements is not required herein.

In some embodiments, the needle guard 50 may comprise a cylindrical member 52 having distal and proximal ends 54 and 56, respectively, as shown in FIG. 1A. The proximal end 56 of the needle guard 50 may be coupled to the housing 12. In the embodiment shown in FIG. 1A, the proximal end 56 of the needle guard 50 is arranged to be coupled within the housing 12 such that a substantial portion of the needle guard 50 extends through the open distal end 14 of the housing 12 in a fully extended position. A biasing element 57, such as a coil spring, may be provided to bias the needle guard 50 in a fully extended position. The biasing element 57 may be disposed between the proximal end 56 of the needle guard 50 and an abutment 12 a provided on an inner surface 12 i of the housing 12.

The device 10 may be operated by placing the needle guard 50 against the skin at the injection site, and then pressing the device toward the skin, which moves the needle guard 50 from the fully extended position in which the injection needle 24 is fully surrounded by the needle guard 50 to a substantially retracted position relative to the housing 12, which at least partially exposes the injection needle 24 and allows it to penetrate the skin at the injection site. In the embodiments where the needle guard 50 also activates the device 10, the movement of the needled guard 50 from the fully extended position to the substantially retracted position activates the device 10. As the device 10 is withdrawn from the injection site, after completion of the injection, the biasing element 57 returns the needle guard 50 back to the fully extended position.

Figure 2:
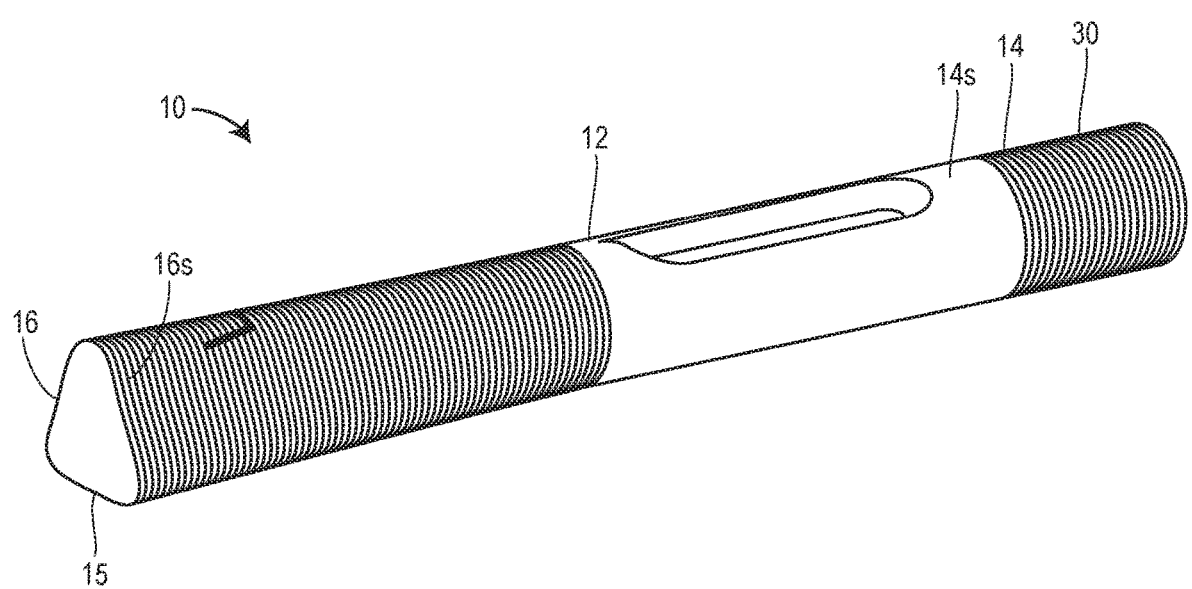
FIG. 2 is a perspective view of the drug injection device according to an embodiment of the disclosure.

As shown in FIG. 2, the housing 12 may be configured so that the distal end 14 thereof and the cap 30 have a first shape 14 s (e.g., cylindrical) and the proximal end 16 thereof has a second shape 16 s (e.g., triangular prism) which is different from the first shape 14 s to distinguish distal and proximal ends 14, 16 of the device 10 from one another. In some embodiments, the shape of the housing 12 may gradually change from one of the first and second shapes 14 s, 16 s to the other one of the first and second shapes 14 s, 16 s as one moves between the cap 30 and proximal end 16 of the housing 12. In some embodiments, at least one of the first and second shapes 14 s, 16 s can include one or more flat or substantially flat surfaces 15 to prevent the device 10 from rolling when placed on a support surface.

Figure 3A:
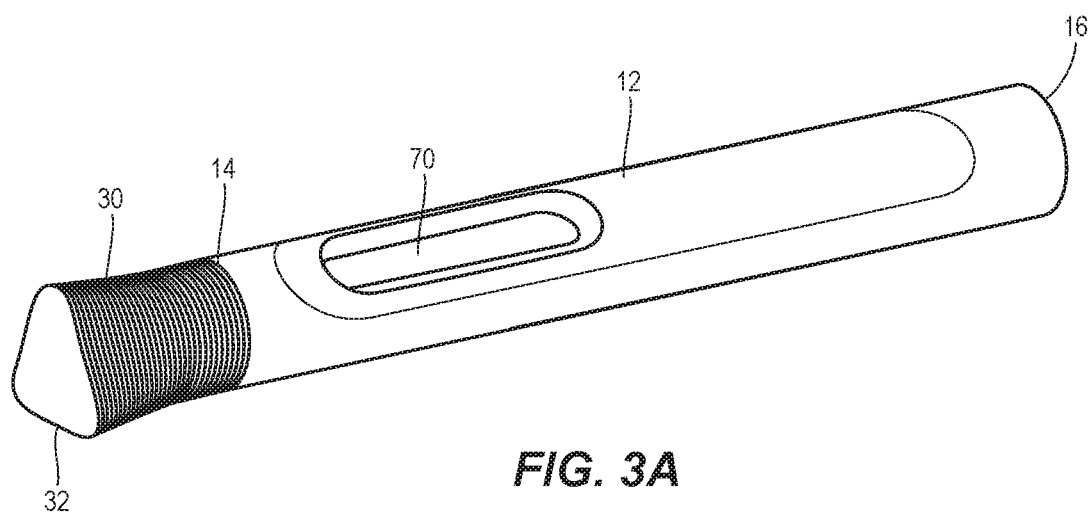
FIG. 3A is a perspective view of the drug injection device according to another embodiment of the disclosure.
Figure 3B:
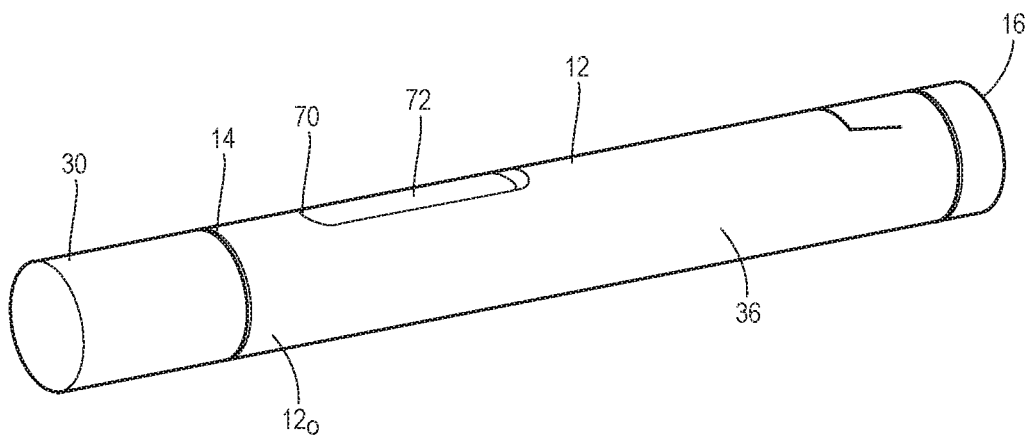
FIG. 3B is a perspective view of the drug injection device according to another embodiment of the disclosure.
Figure 3C:
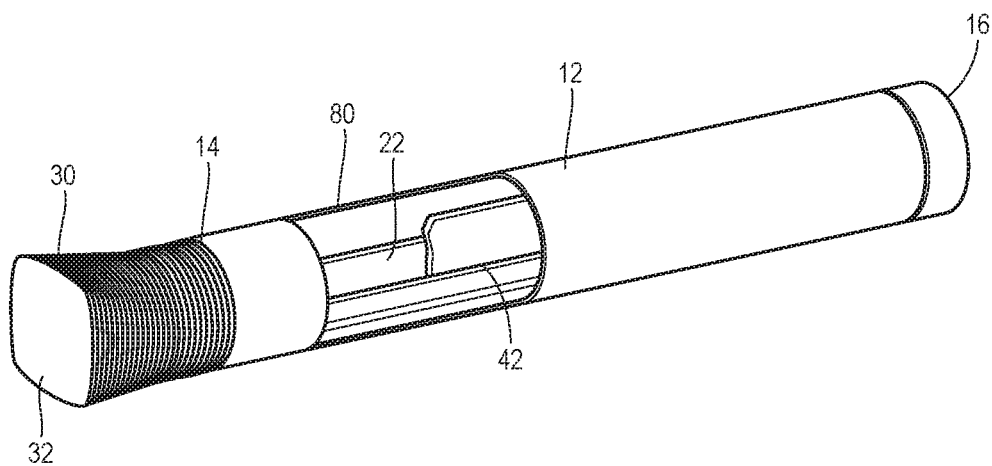
FIG. 3C is a perspective view of the drug injection device according to another embodiment of the disclosure.

Alternatively, as shown in FIGS. 3A and 3C, just the removable cap 30 may be configured with one or more substantially flat surfaces 32 to prevent rolling of the device 10 when placed on a support surface and/or to distinguish the distal end 14 of the device 10 from the proximal end 16 of the device 10.

As shown in FIG. 3B, some embodiments of the device 10 may include a label or grip 36 with non-slip features (e.g., nubs, texturing, grooves, etc.) attached to an outer surface 12 o of the housing 12. The non-slip features facilitate easy gripping of the device and may also identify the end of the device 10. The non-slip features may also be molded into the outer surface 12 o of the housing 12.

In various embodiments of the device 10, as shown in FIG. 3A, the housing 12 may include two, opposing windows 70 (only one is visible) that allow the primary container 20, the drug 22 and the plunger 42 to be viewed by the patient or user from either side of the device 10 during the operation thereof. In such embodiments, the plunger 42 operates to visually indicate the start, progress, and/or completion of the drug injection/extrusion process. As shown in FIG. 3B, the windows 70 in some embodiments may each include a magnifying lens 72, which facilitates easy viewing of the primary container 20, drug 22 and plunger 42 by the patient or user. In other embodiments of the device, the housing 12 may include a single window 70.

Instead of the windows 70 shown in FIGS. 3A and 3B, some embodiments of the device 10 as shown in FIG. 3C may comprise a housing 12 having a transparent housing section 80. The transparent housing section 80 allows 360 degrees of viewing of the primary container 20, drug 22 and plunger 42. Accordingly, the patient or user can easily watch the injection/extrusion process from substantially any angle. The transparent housing section 80 may also be formed to magnify the primary container 20, drug 22 and plunger 42, to facilitate easy viewing thereof.

In some embodiments of the device 10, the plunger 42 may have a vivid color (e.g., green, red, etc.) to facilitate easy viewing thereof via the windows 70 or transparent housing section 80.

Some embodiments of the device 10 may contain a drug 22 that requires refrigeration. Refrigerated drugs often increase the pain of injection. As the drug approaches room temperature, the pain of injection can decrease. Accordingly, various embodiments of the device 10 may include a temperature indicator 34, as shown in FIG. 1A. The temperature indicator 34 may be provided, for example, on or in the housing 12 or cap 30 of the device 10. In other embodiments, the temperature indicator 34 may comprise, for example, a simple binary visual indicator which indicates that the drug 22 is sufficiently close to room temperature so that injection of the drug can be carried out, or a thermometer.

The needle guard 50 and the housing 12 may be configured in some embodiments of the device 10 to visually indicate when injection needle penetration will take place, that correct needle penetration depth has been achieved, when the device 10 will deliver the drug 22, and when the device 10 has completed delivering the drug 22.

Figure 4A:
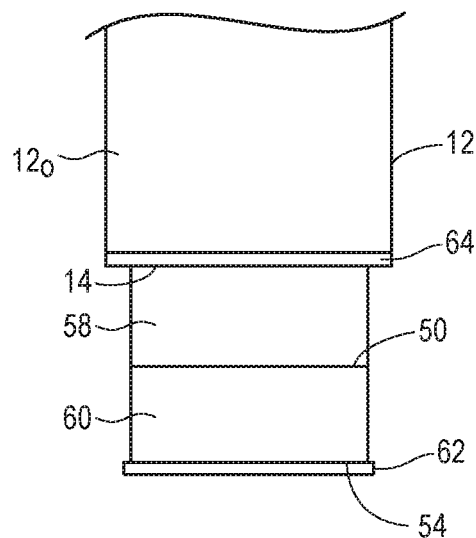
FIG. 4A is a partial elevational view of a needle guard of the drug injection device according to an embodiment of the disclosure.

More specifically, as shown in FIG. 4A, the device 10 in various embodiments may comprise a line or band 64 provided on the outer surface 12 o of the housing 12 at the distal end 14 thereof. Further, the needle guard 50 may comprise distal and proximal outer surface portions 60 and 58, respectively, which are visually distinguished from one another, for example, by color, shade, or some other means. In one embodiment, the distal needle guard surface portion 60 may be a first, vivid color (e.g., green, red, etc.) and the proximal needle guard surface portion 58 may be a second vivid color (e.g., blue, yellow, etc.), which can be easily distinguished from the first, vivid color. The proximal surface portion 58 of the second color may represent a "safe" mode which visually signals or indicates to the patient or user that the injection needle 24 of the device is not contacting or penetrating the skin at the injection site. The distal surface portion 60 of the first color may represent an "action" mode which visually signals or indicates to the patient or user that the injection needle 24 of the device has penetrated the skin at the correct depth. An outer rim 62 may be provided adjacent to the distal end 54 of the needle guard 50. The rim 62 may be the same vivid color as the distal surface portion 60 of the housing 12 or any other suitably vivid color. The band 64 provided on the outer surface 12 o of the housing 12 may be the same color as the distal surface portion 60 of the housing 12 or any other suitable vivid color.

FIGS. 5A-5D depict the operation of the needle guard 50 of FIG. 4A as a visual indicator, wherein at least one indicia disposed on the needle guard 50 provides a visual indication of the position of the needle 24 relative to the injection site based on a position of the needle guard 50 relative to the housing 12 of the device 10.

Figure 5A:
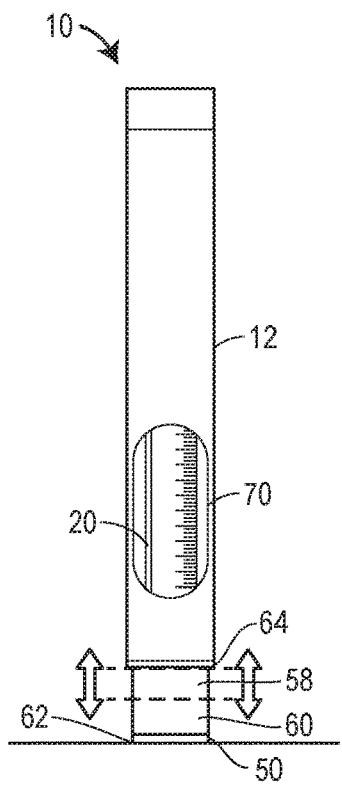
FIGS. 5A-5D are elevational views of the drug injection device showing the operation of the needle guard of FIG. 4A, according to an embodiment of the disclosure.

Referring first to FIG. 5A, the patient or user places the needle guard 50 of the device 10 against the skin at an injection site such that the needle guard 50 is fully extended so that the distal and proximal surface portions 60 and 58, respectively, of the needle guard 50 are exposed outside of the housing and visible. In the fully extended position, the needle guard 50 extends from the housing 12 and beyond the portion of the needle 24 extending out of the housing 12 such that the visible proximal surface portion 58 of the needle guard 50 visually signals or indicates that the injection needle 24 of the device 10 is not making contact with or penetrating the skin at the injection site and therefore, the device 10 is in the safe mode. If the housing 12 of the device 10 includes the earlier described window(s) 70 (shown in FIGS. 5A-5D) or transparent housing section 80, the primary container 20 and the drug 22 may be visible therein in the safe mode. In some embodiments, the plunger 42 may also be visible in the safe mode and located in the proximal portion of the primary container 20. In any case, the image in the window(s) 70 or transparent housing section 80 provides a visual indication that the drug injection/extrusion process has not commenced.

Figure 5B:
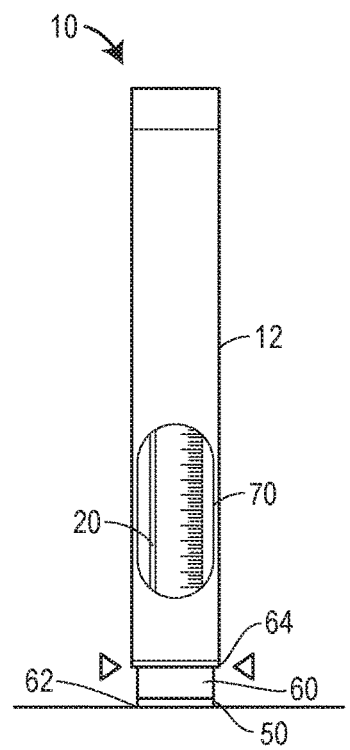
Figure 5C:
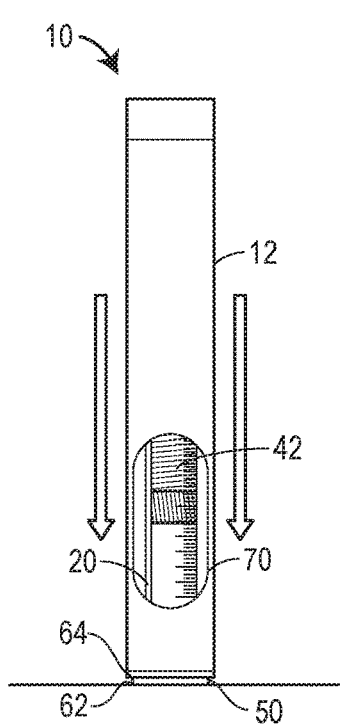

Referring to FIG. 5B, the device 10 has been pressed toward and against the skin at the injection site, which causes the proximal surface portion 58 of the needle guard 50 to move into the distal end 14 of the housing 12, thereby occupying an intermediate position between fully extended (FIG. 5A) and fully retracted positions (FIG. 5C). In this intermediate position, the proximal outer surface portion 58 is concealed inside the housing 12 and the distal outer surface portion 60 is exposed outside of the housing 12. As shown, the device 10 has been pressed toward the skin so that the proximal surface portion 58 of the needle guard 50 is no longer visible and only the distal surface portion 60 of the needle guard 50 is visible. The disappearance of the proximal surface portion 58 of the needle guard 50 visually signals or indicates that further pressing of the device 10 toward the skin will cause the injection needle 24 of the device to penetrate the skin at the injection site thereby placing the device 10 in the action mode. This is because in this intermediate position, the needle guard 50 extends from the housing 12 approximately the same distance that the needle 24 extends out of the housing 12. In addition, the image viewable through the housing window(s) 70 (or transparent housing section 80) visually indicates that the drug injection/extrusion process has not yet commenced. Some embodiments of the device 10 may also be configured with at least one audible indicator mechanism 32 (FIG. 1A), which provides an audible indication when the injection needle 24 is about to penetrate the skin. The audible indicator mechanism 32 can be configured to produce an audible click, one or more beeps, or any other suitable sound, which can be easily heard. The audible indicator mechanism 32 can comprise any suitable mechanical, electrical or electromechanical arrangement for generating the audible indication.

Referring to FIG. 5C, the device 10 has been pressed further toward the skin at the injection site, which causes the distal surface portion 60 of the needle guard 50 to move into the distal end 14 of the housing 12. The device 10 is pressed toward the skin until the distal surface portion 60 of the needle guard 50 is no longer visible except for the rim 62 which engages the band 64 provided on the outer surface 12 o of the housing 12. In this fully retracted position, a substantial portion of the needle 24 extending out of the housing 12 is exposed beyond the needle guard 50 and penetrating the patient, and both the proximal and distal outer surface portions 58, 60 are concealed inside the housing 12. The disappearance of the distal surface portion 60 of the needle guard 50 (except for the rim 62) visually signals or indicates that the correct depth of needle penetration has been achieved and that the drive mechanism 40 has been activated to commence injection/extrusion of the drug 22. Upon commencement of drug the injection/extrusion process, the plunger 42 starts to move through the primary container 20 as can be seen through the housing window(s) 70 (or transparent housing section 80), thereby providing another visual indication that the injection/extrusion process has started. In addition to the aforementioned visual indicators, embodiments of the device 10 configured with the audible indicator mechanism 32 (FIG. 1A) can also provide an audible indication (e.g., one or more clicks, beeps, etc.) that the drive mechanism 40 has been activated to commence injection of the drug 22.

Figure 5D:
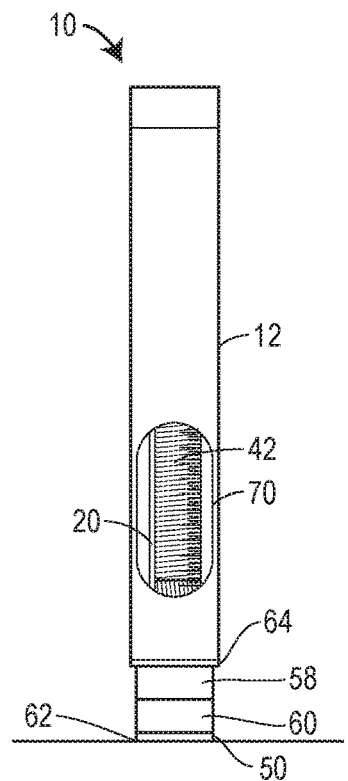

As the drug injection/extrusion process continues, the plunger's 42 movement through the primary container 20 can be viewed by the patient or user through the window(s) 70 (or the transparent housing section 80) of the device housing 12. FIG. 5D shows the device 10 after the completion of the injection/extrusion process and the partial withdrawal of the device 10 from the skin at the injection site. As shown, the plunger 42 substantially fills the window(s) 70 (or transparent housing section 80), thereby visually indicating that the drug injection/extrusion process is completed. Embodiments of the device 10 having the audible indicator mechanism 32 (FIG. 1A) can be configured to also provide an audible indication (e.g., one or more clicks, beeps, etc.) that the drug injection/extrusion process is completed. Withdrawal of the device 10 fully extends the needle guard 50 so that the proximal needle guard surface portion 60 is visible, thereby visually indicating to the patient or user that the device 10 is back in the safe mode where injection needle 24 of the device 10 is no longer penetrating or contacting the skin at the injection site.

Once in the safe mode, the device 10 can be safely removed from the injection site as the needle guard 50 is fully extended and surrounding the injection needle 24. In some embodiments, the device 10 may be configured so that the needle guard 50 locks in place in the fully extended position and cannot thereafter be moved from its locked position in the proximal direction relative to the housing 12 to expose the injection needle 24. The used device 10 is, therefore, rendered safe for handling. In single-use embodiments, the device 10 can now be safely discarded. If configured as a reusable device, the primary container 20 can now be discarded and replaced with a new primary container 20.

Figure 1B:
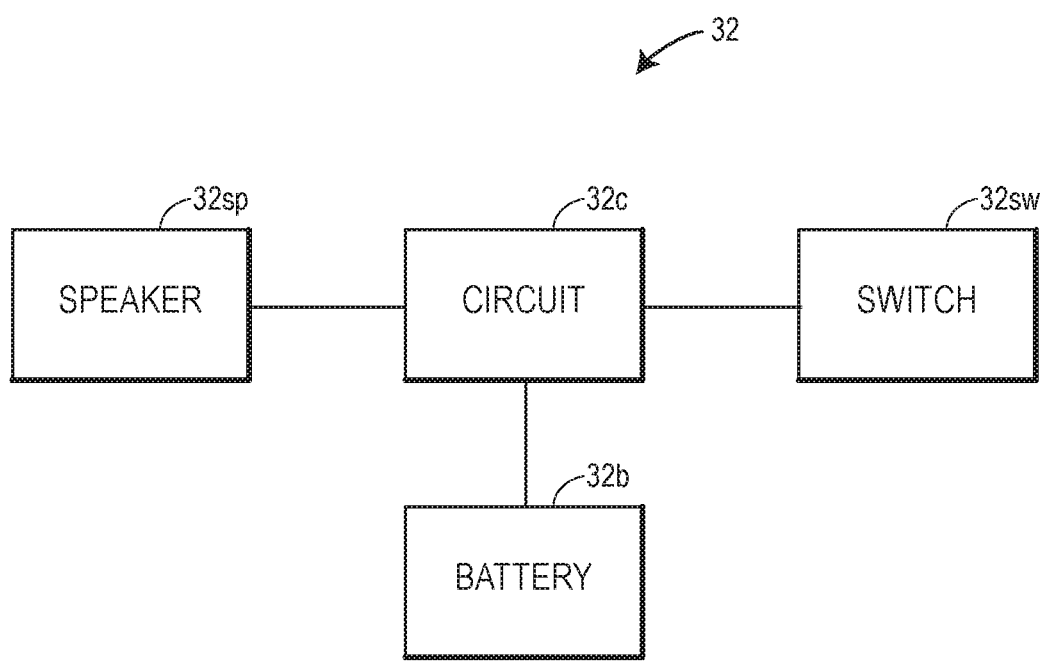
FIG. 1B is a block diagram of an audible indicator mechanism for the injection device according to an embodiment of the disclosure.

Referring to FIG. 1B, the audible indicator mechanism 32 mentioned earlier may comprise a speaker 32 *sp*, a circuit 32 *c* for driving the speaker 32 *s*, a battery 32 *b* for powering the circuit 32 *c*, and a switch 32 *sw* for activating the circuit 32 *c*. The switch 32 *sw* may be activated by the motion of the needle guard 50. The speaker 32 *sp* may be similar to a cell phone speaker, which typically uses an electromagnet or small crystal to generate the vibrations. In some embodiments, the circuit 32 *c* may include a read only memory for storing tone data, music, and/or other sounds. The circuit 32 *c* may also include logic for converting the tone data, music, and/or other sounds, to a signal that vibrates the speaker 32 *sp* and timing logic for stepping through the memory. The switch 32 *sw* may comprise one of a reed switch, a capacitance switch, an impedance switch, and any other suitable switch that is capable of transducing the motion of the needle guard 50.

Figure 4B:
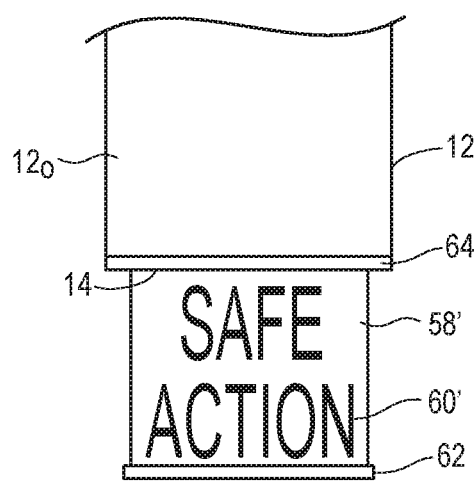
FIG. 4B is a partial elevational view of the needle guard of the drug injection device according to another embodiment of the disclosure.

FIG. 4B shows another embodiment of the needle guard 50', which includes text-based indicia instead of color for visually indicating when the device 10 is in the safe mode and when the device 10 is in the action mode, described earlier. The text-based indicia may comprise one or more occurrences of a word such as "SAFE" or any other suitable word or phrase disposed on the proximal outer surface portion 58' of the needle guard 50' and one or more occurrences a word such as "ACTION" and/or any other suitable word or phrase disposed on the distal outer surface portion 60' of the needle guard 50'.

In various other embodiments, the needle guard may include both color- and text-based indicia for visually indicating when the device is in the safe mode and when the device is in the action mode as described earlier. Alternatively, the needle guard may include image-based indicia for visually indicating when the device is in the safe mode and when the device is in the action mode as described earlier. The image-based indicia may comprise one or more occurrences of an image or symbol representing the safe mode on the proximal outer surface portion of the needle guard and one or more occurrences an image or symbol representing the action mode on the distal outer surface portion of the needle guard. The image-based indicia may also be combined with the color- and/or text-based indicia described earlier. In various other embodiments, distal and proximal portions of the needle guard may be configured so that they can include symbols, graphics, patterns, or any other visual indication to indicate the safe and action modes. The selected indication of the needle guard may be combined with any combination of the above-mentioned visual and audible indicators. In various other embodiments, distal and proximal portions of the needle guard may be configured so that they can be selectively illuminated to indicate the safe and action modes. The selected illumination of the needle guard may be combined with any combination of the above-mentioned visual and audible indicators.

FIG. 6A shows another embodiment of the device 10 comprising a telescoping needle guard denoted by reference numeral 90 occupying a fully extended position. The telescoping needle guard 90 may comprise proximal (e.g., first) and distal (e.g., second) needle guard members 98 and 100, respectively, each having an outer surface exposed outside of the housing 12 in FIG. 6A. An outer rim 92 may be disposed adjacent to a distal end 100 *d* of the distal needle guard member 100. The proximal needle guard member 98 can be biased in a fully extended position with the same biasing element 57 used to bias the previously described needle guards. A second biasing element 96, such as a coil spring, may be provided to bias the distal needle guard member 100 in a fully extended position with respect to the proximal needle guard member 98. The second biasing element 96 should provide a lower biasing force than biasing element 57, so that the distal needle guard member 100 moves from the fully extended position to a fully collapsed (e.g., retracted) position before the proximal needle guard member 98 moves from the fully extended position to a fully collapsed (e.g., retracted) position within the housing 12. The biasing element 96 may be disposed between an abutment 100 *a* provided on an inner surface 100 *i* of the distal needle guard member 100 adjacent to the distal end 100 *d* thereof and a distal edge surface 98 *es* of the proximal needle guard member 98. The distal and proximal needle guard members 98, 100 can be configured with the color-, text-, image-based, and illuminated visual indicators described earlier.

As shown in FIGS. 6B and 6C, the telescoping needle guard 90 operates in a manner similar to the needle guards described earlier and in conjunction with the previously described audible indicators, except that when the device 10 is pressed toward and against the skin at the injection site, the distal needle guard member 100 slides over the proximal needle guard member 98 until it is no longer visible and only the distal needle guard member 100 of the telescoping needle guard 90 is visible, as shown in FIG. 6C. In this intermediate position depicted in FIG. 6C, the outer surface of the proximal needle guard member 98 is concealed inside the distal needle guard member 100, which itself remains exposed outside of the housing 12. Similar to the needle guards described earlier, the disappearance of the proximal needle guard member 98 visually indicates that further pressing of the device 10 toward the skin will cause the injection needle 24 of the device to penetrate the skin at the injection site thereby placing the device 10 in the action mode.

As shown in FIG. 6D, when the device 10 is pressed further toward the skin at the injection site, the distal needle guard member 100 and the proximal needle guard member 98 disposed and concealed within the distal needle guard member 100, both move together into the distal end 14 of the housing 12 until the distal needle guard member 100 is no longer visible except for the rim 92, which engages the band 64 provided on the outer surface 12 o of the housing 12. In this fully retracted position, the outer surfaces of the proximal and distal needle guard members 98 are concealed inside the housing 12. As with the needle guards described earlier, the disappearance of the distal needle guard member 100 (except of the rim 92) visually indicates that the correct needle penetration depth has been achieved and the drive mechanism 40 has been activated to commence injection/extrusion of the drug 22.

Figure 7A:
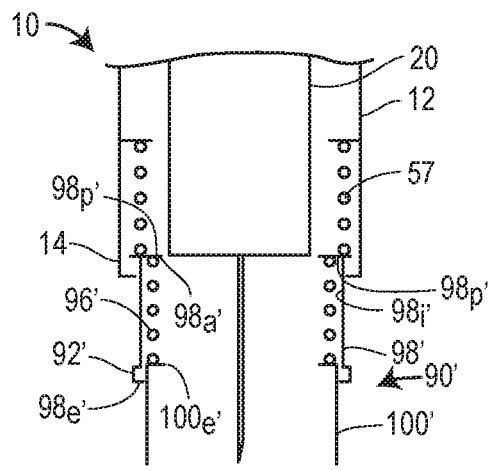
FIG. 7A is a partial elevational view of a needle guard of the drug injection device according to another embodiment of the disclosure.

FIG. 7A shows another embodiment of the device 10 comprising an alternate version of the telescoping needle guard denoted by reference numeral 90' occupying a fully extended position. The telescoping needle guard 90' is similar to the telescoping needle guard 90 of FIGS. 6A-6D, except the distal and proximal needle guard members 98', 100' are configured so that the distal needle guard member 100' collapses into and inside of the proximal needle guard 98' in the intermediate and fully retracted positions, instead of over it as in the telescoping needle guard of FIGS. 6A-6C. Further, an outer rim 92' is provided on the proximal needle guard member 98' adjacent to the distal end 98 e' thereof. A second biasing element 96', such as a coil spring, may be provided to bias the distal needle guard member 100' in a fully extended position with respect to the proximal needle guard member 98'. The biasing element 96' may be disposed between a proximal edge surface 100 e' of the distal needle guard member 100' and an abutment 98 a' provided on an inner surface 98 i' of the proximal needle guard member 98' adjacent to a proximal end 98 p' thereof. The second biasing element 96' should provide a lower biasing force than biasing element 57 so that the distal needle guard member 100' moves from the fully extended position to a fully collapsed (e.g., retracted) position before the proximal needle guard member 98' moves from the fully extended position to a fully collapsed (e.g., retracted) position within the housing 12. The distal and proximal needle guard members 98', 100' can be configured with the color-, text-, image-based, and illuminated visual indicators described earlier.

Figures 7B, 7C, 7D:
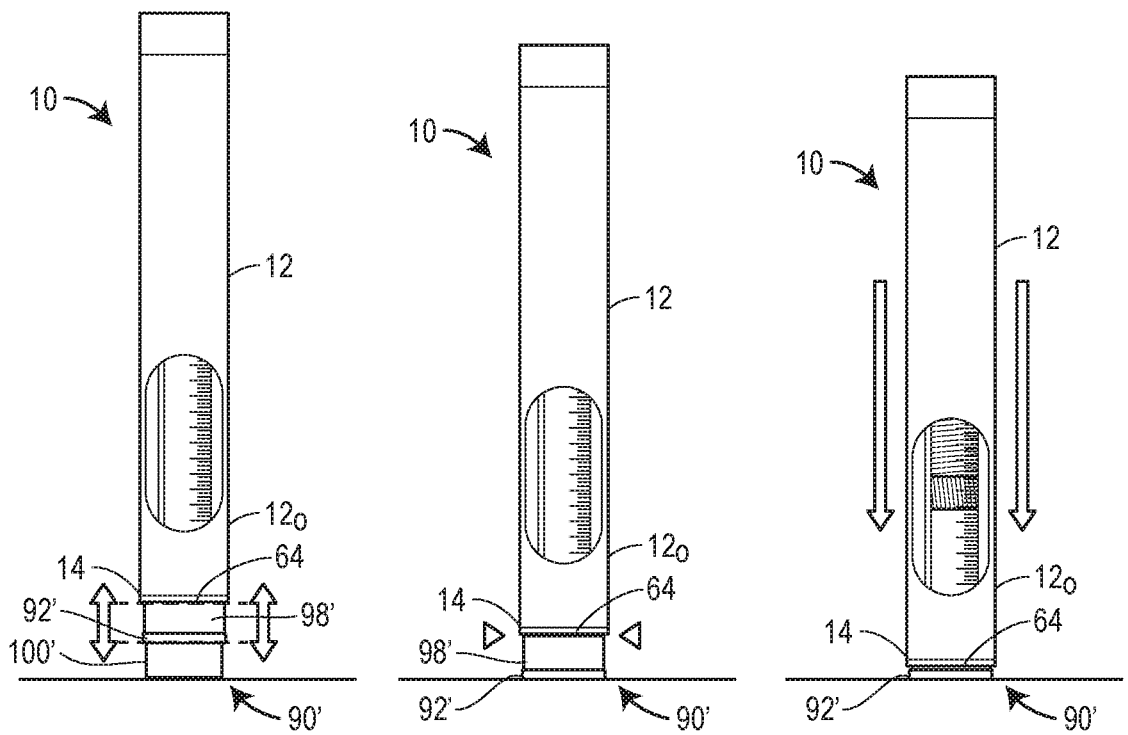
FIGS. 7B-7D are elevational views of the drug injection device showing the operation of the needle guard of FIG. 7A, according to an embodiment of the disclosure.

As shown in FIGS. 7B-7D, the telescoping needle guard 90' operates in a manner similar to the previously described needle guards and in conjunction with the previously described audible indicators, except when the device 10 is pressed toward and against the skin at the injection site, the distal needle guard member 100' slides into the proximal needle guard member 98' until it is no longer visible and only the proximal needle guard member 98' of the telescoping needle guard 90' is visible. Further, in contrast to the previously described needle guards, the disappearance of the distal needle guard member 100' visually indicates that further pressing of the device 10 toward the skin will cause the injection needle 24 of the device to penetrate the skin at the injection site thereby placing the device 10 in the action mode.

In FIG. 7B, the needle guard 90' occupies the fully extended position whereby the outer surfaces of the proximal and distal needle guard members 98', 100' are exposed outside of the housing 12. Further, as shown in FIG. 7C, the needle guard 90' moves into an intermediate position when the device 10 is pressed further toward the skin at the injection site and the distal needle guard member 100' becomes disposed and concealed within the proximal needle guard member 98'. Further force applied to the device 10 causes both the proximal and distal needle guard members 98', 100' to move together into and become concealed within the distal end 14 of the housing 12. In this fully retracted position depicted in FIG. 7D, the proximal needle guard member 98' is no longer visible except for the rim 92', which engages the band 64 provided on the outer surface 12 o of the housing 12. In further contrast to the previously described needle guards, the disappearance of the proximal needle guard member 98' (except for the rim 92') visually indicates that the correct needle penetration depth has been achieved and the drive mechanism 40 has been activated to commence injection/extrusion of the drug 22.

Figure 8:
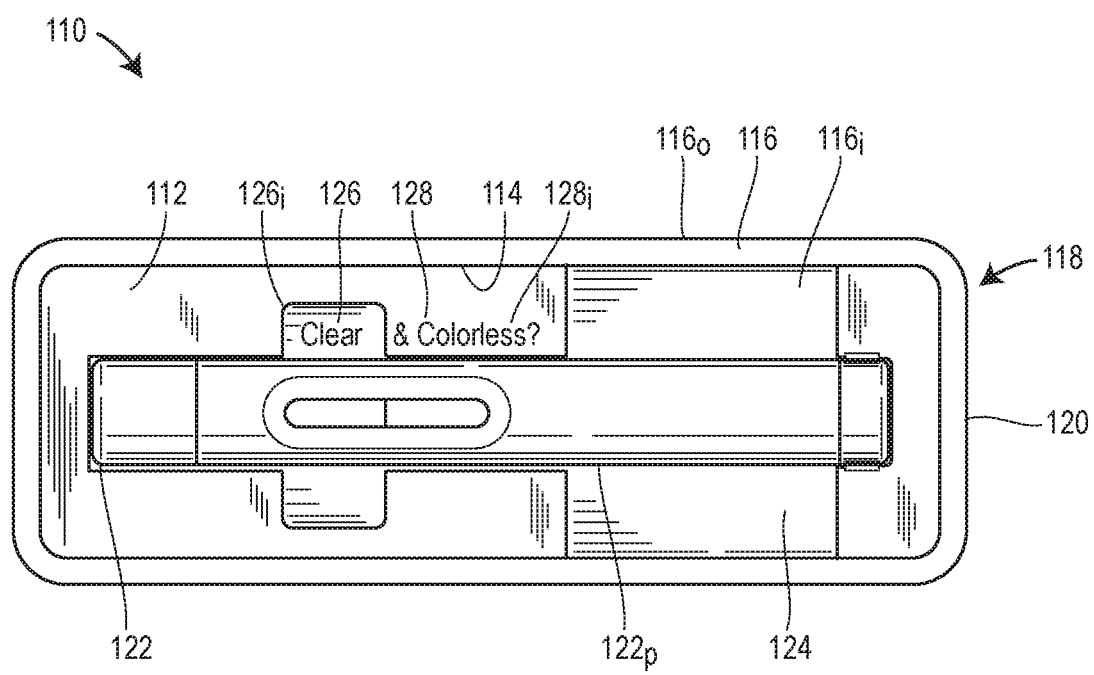
FIG. 8 is a plan view of a tray according to an embodiment of the disclosure, for confirming the quality of the drug contained within the drug injection device.

Referring now to FIG. 8, there is shown an embodiment of a drug injection device tray according to the present disclosure, denoted generally by reference numeral 110. The tray 110 may be used for allowing the patient or user to visually confirm that the drug 22 contained in the primary container 20 of the device 10 is particle-free (clear) and/or colorless. The tray 110 may also be used with any other drug injection device which allows viewing of the drug contained therein. Further, the tray may 110 also be used for packaging the drug injection device 10 or any other drug injection device.

As shown in FIG. 8, various embodiments of the tray 110 may comprise a flat, elongated, support wall 112 with inner side walls 114 extending between the support wall 112 and an inner edge 116 i of a rim surface 116 extending about an outer periphery 118 of the tray 110 above the support wall 112. Outer side walls 120 may extend from an outer edge 116 o of the rim surface 116 to support the tray 110. The support wall 112 may include a first recess 122 shaped and dimensioned for securely receiving the drug injection device 10 or any other injection device. The support wall 112 may further include a second recess 124 extending transversely to the first recess 122, which allows the patient or user to grip the device 10 with their fingers and remove it from the first recess 122 of the tray 110. The second recess 124 may be configured as shown to communicate with a portion 122 p of the first recess so that the fingers can reach under the device 10 and grasp it. The first and second recesses 122, 124 may be configured so that they do not extend below supporting edges (not visible) of the outer side walls 120 of the tray 110. The tray 110 may be made from any suitable material including folded sheet metal and injection molded plastic.

Still referring to FIG. 8, the first recess 124 may include a first drug test surface 126. The first drug test surface 126 may be located at least partially under an adjacent one of the opposing windows 70 (shown in FIG. 8) or a portion of the transparent housing section 80 (not shown) of the device housing 12 when the device 10 is seated in the first recess 122. The first drug test surface 126 optionally extends onto the support wall 112 as shown in FIG. 8. The first drug test surface 126 may, for example, comprise an adhesively bonded label or be a unitarily formed section of the first recess 122 (and support wall 112). The first drug test surface 126 may be configured for determining or checking the clarity of the drug 22 (shown in FIG. 8) or the color of the drug 22. The patient or user can make this determination by viewing the drug 22 through the window(s) 70 or the transparent housing section 80 of the device housing 12 and comparing the drug 22 with the drug test surface 126, which forms a background for the drug 22. When determining or checking the clarity of the drug 22 (shown in FIG. 8), the first drug test surface 126 may be configured as a dark color (e.g., black), which allows easy visual identification of particles and/or cloudiness in the drug 22 if, for example, the drug should be clear. The first drug test surface 126 may also include text- and/or image-based indicia 126 *i* that instruct the patient or user to check the clarity of the drug 22. When determining or checking the color of the drug 22, the drug test surface 126 may be configured as a light color (e.g., white), which allows easy visual identification of whether the drug 22 is colored if, for example, the drug 22 should be colorless. The first drug test surface 126 may also include text- and/or image-based indicia (not shown) that instruct the patient or user to check the color of the drug 22.

The first recess 124 may further include a second drug test surface 128. The second test surface 128 may be located next to the first drug test surface 126 under another portion of the adjacent window 70 (shown in FIG. 8) or transparent housing section 80 (not shown) of the device housing 12 when the device 10 is seated in the first recess 122. The second drug test surface 128 may optionally extend onto the support wall 112 as shown in FIG. 8. The second drug test surface 128 may, for example, comprise an adhesively bonded label or be a unitarily formed section of the first recess 122 (and support wall 112). The second drug test surface 128 may be configured for determining or checking the clarity of the drug 22 or the color of the drug 22 (shown in FIG. 8), as described earlier where the patient or user views the drug 22 through the window(s) 70 or portion of the transparent housing section 80 of the device housing 12 and comparing the drug 22 with the second drug test surface 128, which forms a background for the drug 22. When determining or checking the clarity of the drug 22, the second drug test surface 128 may be configured as a dark color (e.g., black), which allows easy visual identification of particles and/or cloudiness in the drug 22 if, for example, the drug should be clear. The second drug test surface 128 may also include text- and/or image-based indicia (not shown) that instruct the patient or user to check the clarity of the drug 22. When determining or checking the color of the drug 22 (shown in FIG. 8), the second drug test surface 128 may be configured as a light color (e.g., white), which allows easy visual identification of whether the drug 22 is colored if, for example, the drug 22 should be colorless. The second drug test surface 128 may also include text- and/or image-based indicia 128 *i* that instruct the patient or user to check the color of the drug 22.

Figure 9A:
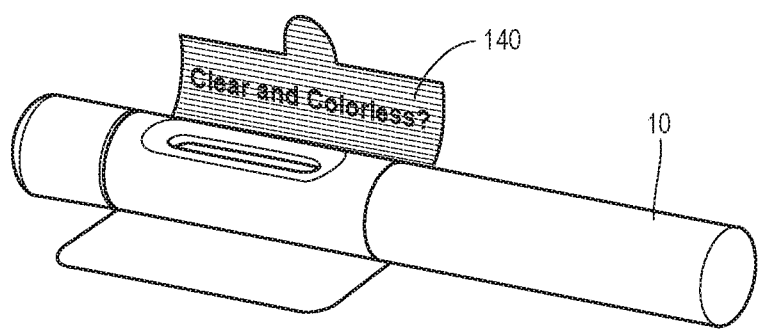
FIG. 9A is a perspective view of the drug injection device having a label (shown in an open state) for confirming the quality of the drug contained within the drug injection device, according to an embodiment of the disclosure.
Figure 9B:
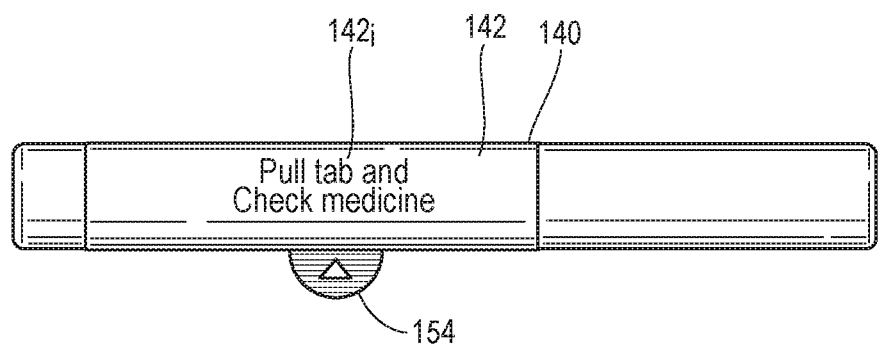
FIG. 9B is a plan view of the drug injection device of FIG. 9A, which shows the label wrapped around the device prior to its use to confirm the quality of the drug.
Figure 9C:
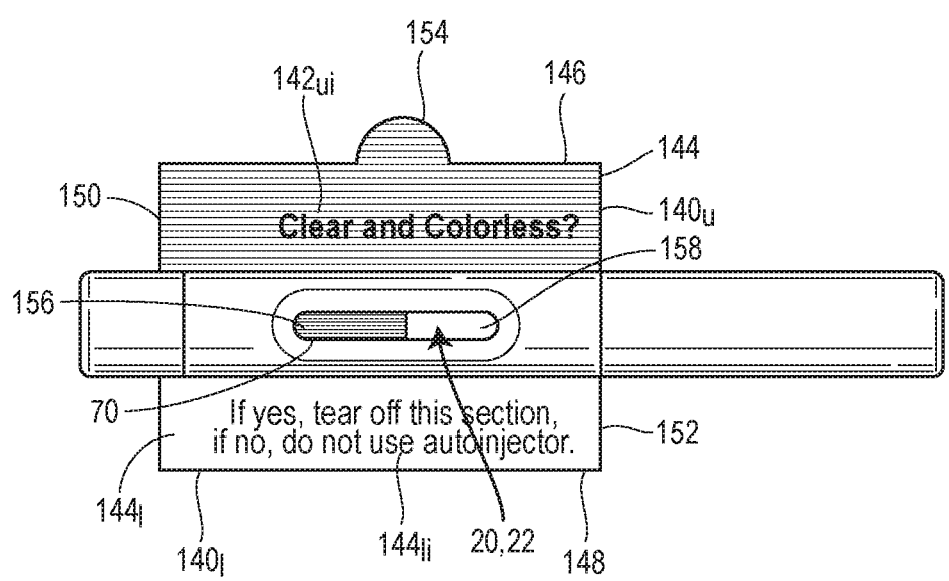
FIG. 9C is a plan view of the drug injection device of FIG. 9B, which shows the label in an open position, which allows it to be used to confirm the quality of the drug contained within the drug injection device.

Referring now to FIGS. 9A-9C, there is shown an embodiment of the injection device with a removable drug injection device label according to the present disclosure. The label is denoted generally by reference numeral 140. The label 140 allows the patient or user to observe the drug 22 (FIG. 9C) contained in the primary container 20 of the device 10 and confirm that it is particle-free (clear) and/or colorless. The label 140 may also serve as a tamper indicator for indicating whether the drug injection device 10 has been tampered with or previously used. It is contemplated that the label 140 can be used with any drug injection device that allows viewing of the drug contained therein.

As best shown in FIG. 9C, the removable label 140 includes a top edge 146, a bottom edge 148, and first and second side edges 150 and 152, respectively, an outer surface 142 (FIG. 9B), an inner surface 144. A pull tab 154 may be provided on the top edge 146 (shown in FIGS. 9A-9C) or the bottom edge 148 of the label 140 for facilitating the opening or peeling of the label 140.

As shown in FIG. 9B, the label 140 wraps around the housing 12 of the device 10 so that the inner surface 144 of the label 140 covers both the windows 70 (shown in FIGS. 9A and 9C) or the transparent housing section 80 (not shown) of the device housing 12. The label 140 may be configured to also wrap around a proximal portion of the cap 30 of the device 10, thereby serving as a tamper indicator for indicating whether the drug injection device 10 has been tampered with or previously used. The inner surface 144 of the label 140 may include an adhesive (not shown) for removably bonding the label to the housing 12 (and the cap 30).

As shown in FIG. 9B, the outer surface 142 of the label 140 may include text- and/or image-based indicia 142 *i* that instruct the patient or user to pull the tab 154 and check the drug contained in the primary container of the device 10.

As best shown in FIG. 9C, an intermediate section of the inner surface 144 of the label 140 may include a first drug test surface 156. When the label 140 is applied to the device 10, the first drug test surface 156 is located at least partially under an adjacent one of the opposing windows 70 (shown in FIG. 9C) or the transparent housing section 80 (not shown) of the device housing 12. The first drug test surface 156 may be configured for determining or checking the clarity of the drug 22 (shown in FIG. 9C) or the color of the drug 22. The patient or user can make this determination by grasping the pull tab 154 and peeling back an upper portion 140 *u* of the label 140 from the housing 12 to reveal one of the windows 70 (shown in FIG. 9C) or the transparent housing section 80 (not shown) of the device housing 12. The drug, which is visible through the revealed window 70 or the portion of the transparent housing section 80 of the device housing 12 facing the patient or user, can then be compared with the first drug test surface 156, which forms a background for the drug 22. When determining or checking the clarity of the drug 22 (shown in FIG. 9C), the first drug test surface 156 may be configured as a dark color (e.g., black), which allows easy visual identification of particles and/or cloudiness in the drug 22 if, for example, the drug 22 should be clear. When determining or checking the color of the drug 22, the drug test surface 156 may be configured as a light color (e.g., white), which allows easy visual identification of whether the drug 22 is colored if, for example, the drug 22 should be colorless. The inner surface 144 *u* of the upper portion 140 *u* of the label 140 may also include text- and/or image-based indicia 144 *ui* that instruct the patient or user to check the clarity of the drug 22 (shown in FIG. 9C) or the color of the drug 22.

As best shown in FIG. 9C, the intermediate section of the inner surface 144 of the label 140 may also include a second drug test surface 158. The second drug test surface 158 may be located next to the first drug test surface 156 under a portion of the adjacent one of the opposing windows 70 (shown in FIG. 9C) or the transparent housing section 80 (not shown) of the device housing 12. The second drug test surface 158 may be configured for determining or checking the clarity of the drug 22 or the color of the drug 22 (shown in FIG. 9C) after the upper portion 140 u of the label 140 has been pulled back from the housing to reveal one of the windows 70 (shown in FIG. 9C) or the portion transparent housing section 80 (not shown) of the device housing 12, as described earlier. The drug 22 can then be compared with the second drug test surface 158, which forms a background for the drug 22. When determining or checking the clarity of the drug 22, the second drug test surface 158 may be configured as a dark color (e.g., black), which allows easy visual identification of particles and/or cloudiness in the drug 22 if, for example, the drug should be clear. When determining or checking the color of the drug 22 (shown in FIG. 9C), the second drug test surface 158 may be configured as a light color (e.g., white), which allows easy visual identification of whether the drug 22 is colored if, for example, the drug 22 should be colorless.

The label 140 may be dimensioned so that a lower portion 1401 of the label 140 is covered by the upper portion 140 u of the label 140 (shown in FIG. 9B) prior to peeling or unwrapping. In addition the inner surface 1441 of the lower portion 1401 of the label 140 may be devoid of adhesive. Therefore, when the upper label portion 140 u is peeled back to check the drug 22, the lower label portion 1401 releases from the housing 12 (and cap 30) as shown in FIGS. 9A and 9C. The inner surface 1441 of the lower label portion 1401 may include text- and/or image-based indicia 1441 i that instruct the patient or user regarding whether the use of the injector after checking the drug 22. For example the indicia 1441 i may instruct the patient or user to remove the label 140 from the device 10 if the drug 22 is clear and/or colorless, or not use the device 10 if the drug 22 is not clear and/or not colorless.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a container of the device. In some instances, the container is a primary container that is either filled or pre-filled for treatment with the medicament. The primary container can be a cartridge or a pre-filled syringe.

For example, the drug delivery device or more specifically the container of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858) as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, Myostatin binding proteins, peptibodies, and related proteins, and the like, including myostatin specific peptibodies, particularly those described in U.S. Publication No. 2004/0181033 and PCT Publication No. WO 2004/058988, particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1;

Interleukin 1-receptor 1 ("IL1-R1") specific antibodies, peptibodies, and related proteins, and the like, including but not limited to those described in U.S. Publication No. 2004/097712, in parts pertinent to IL1-R1 specific binding proteins, monoclonal antibodies in particular, especially, without limitation, those designated therein: 15CA, 26F5, 27F2, 24E12, and 10H7;

Ang2 specific antibodies, peptibodies, and related proteins, and the like, including but not limited to those described in PCT Publication No. WO 03/057134 and U.S. Publication No. 2003/0229023, in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8 (N); TN8-14 (N); Con 1 (N), also including anti-Ang 2 antibodies and formulations such as those described in PCT Publication No. WO 2003/030833, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein;

NGF specific antibodies, peptibodies, and related proteins, and the like including, in particular, but not limited to those described in U.S. Publication No. 2005/0074821 and U.S. Pat. No. 6,919,426, as to NGF-specific antibodies and related proteins in this regard, including in particular, but not limited to, the NGF-specific antibodies therein designated 4D4, 4G6, 6H9, 7H2, 14D10 and 14D11;

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT- 11A5, PINT-11A7, PINT-11A12, PINT-12A1, PINT-12A2, PINT-12A3, PINT-12A4, and PINT-12A5, as described therein, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein);

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing publication and in Thakur et al. (1999), Mol. Immunol. 36:1107-1115. In addition, description of the properties of these antibodies provided in the foregoing publication. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, as to TALL-1 binding proteins, particularly the molecules of Tables 4 and 5B;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-la); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 14687-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, tray, elements thereof, methods, and systems have been described in terms of illustrative embodiments, they are not limited thereto. Rather, the appended claims should be construed broadly to include other variants and embodiments of same, which may be made by those skilled in the art without departing from the scope and range of equivalents of the device, tray, elements methods, and systems.

What is claimed is:

1. A drug injection device comprising:
a housing for holding a container, the container storing a drug therein, the housing including at least one window that allows viewing of the drug in the container; and
a drug test surface removably disposed over at least a portion of the housing and immediately adjacent to at least a portion of the at least one window in the housing, such that the drug in the container can be compared against the drug test surface to determine at least one of a clarity or a color of the drug by viewing the drug against the drug test surface through the at least one window of the housing.

2. The drug injection device of claim 1, wherein the at least one window comprises two or more discrete windows that allow viewing of the drug in the container.

3. The drug injection device of claim 1, wherein the at least one window comprises a transparent 360 degree section of the housing of the container.

4. The drug injection device of claim 1, wherein the drug test surface is provided by a removable label, the label having first and second sections, the second section of the label that defines the drug test surface.

5. The drug injection device of claim 4, wherein the drug test surface of the second section includes an area of a first color for testing one of the clarity or the color of the drug.

6. The drug injection device of claim 5, wherein the drug test surface of the second section includes an area of a second color for testing the other one of the clarity or the color of the drug.

7. The drug injection device of claim 4, wherein the label covers at least a portion of the at least one window.

8. The drug injection device of claim 7, wherein the second section of the label includes an inner surface that defines the drug test surface; and removal of the first section of the label from the housing exposes the drug test surface of the second section of the label to be visible through the at least one window.

9. The drug injection device of claim 4, wherein the first section of the label has a first instruction to remove the first section to check the drug and a second instruction to determine the at least one of the clarity or the color of the drug.

10. The drug injection device of claim 9, wherein the label further includes a third section having a first instruction to remove the third section of the label if the at least one of the clarity or the color of the drug is determined to be proper and a second instruction to not use the device if the at least one of the clarity or the color of the drug is determined to be improper.

11. The drug injection device of claim 4, wherein the label includes a pull tab.

12. The drug injection device of claim 4, wherein the container includes a needle for penetrating skin and dispensing the drug stored in the container, at least a portion of the needle extending out of the housing and further comprising a cap for enclosing the at least portion of the needle.

13. The drug injection device of claim 12, wherein the label at least partially covers the cap acting as a tamper evident feature.

* * * * *